United States Patent [19]

Reutelingsperger

[11] Patent Number: 5,834,196
[45] Date of Patent: Nov. 10, 1998

[54] METHOD FOR DETECTING AND/OR OPTIONALLY QUANTIFYING AND/OR SEPARATING APOPTOTIC CELLS IN OR FROM A SAMPLE

[75] Inventor: Christiaan Peter Maria Reutelingsperger, Maastricht, Netherlands

[73] Assignee: Nexins Research B.V., Netherlands

[21] Appl. No.: 727,506

[22] PCT Filed: Apr. 11, 1995

[86] PCT No.: PCT/NL95/00134

§ 371 Date: Oct. 11, 1996

§ 102(e) Date: Oct. 11, 1996

[87] PCT Pub. No.: WO95/27903

PCT Pub. Date: Oct. 19, 1995

[30] Foreign Application Priority Data

Apr. 11, 1994 [EP] European Pat. Off. ............... 94200968

[51] Int. Cl.$^6$ ............................. C12Q 1/68; G01N 33/567
[52] U.S. Cl. ............................. 435/6; 435/7.21; 435/30; 436/546
[58] Field of Search ............................. 435/6, 7.21, 7.23, 435/7.24, 7.5, 7.8, 7.9, 30, 176, 968, 975; 436/518, 519, 545, 546

[56] References Cited

U.S. PATENT DOCUMENTS 5,627,036  5/1997  Reutelingsperger .................... 435/7.21

OTHER PUBLICATIONS

Tait et al; "Phospholipid Binding Properties of Human Placental Anticoagulant Protein–I, a Member of the Lipocortin Family", Journal of Biological Chemistry, 264 (14): 7044–49, May 15, 1989.

Andree et al., "Binding of Vascular Anticoagulant α (VACα) to Planar Phospholipid Bilayers", Journal of Biological Chemistry, 256(9): 4923–4928, Mar. 25, 1990.

Fadok et al., Exposure of phosphatidylserine on the surface of apoptotic lymphocytes triggers specific recognition by macrophages, J. Immunol. 148(7):2207–2216, 1992.

Umeda et al., Effective production of monoclonal antibodies against phosphatidylserine: stereo–specific recognition of phosphatidylserine by monoclonal antibody, J. Immunol. 143(7):2273–2279, 1989.

Rote et al., Immunologic detection of phosphatidylserine externalization during thrombin–induced platelet activation. Clin. Immunol. Immunopathol. 66(3):193–200, 1993.

Thiagarajan et al., Binding of Annexin V/Placental Anticoagulant Protein I to Platelets. Evidence for phosphatidylserine exposure in the procoagulant response of activated platelets. J. Biol. Chem. 265(29):17420–17423, 1990.

*Primary Examiner*—Marian C. Knode
*Assistant Examiner*—Donna C. Wortman
*Attorney, Agent, or Firm*—Cushman Darby & Cushman IP Group of Pillsbury Madison & Sutro LLP

[57] ABSTRACT

A procedure to measure apoptosis in physiology and pathology in order to support clinical diagnosis and monitor efficacies of drugs and therapies. In particular a method for detecting and/or optionally quantifying and/or optionally isolating apoptotic cells in a sample, comprising contacting the sample with a detectable reagent having high affinity for phosphatidyl serine; and qualitatively and/or optionally quantitatively detecting cells that have reacted with the detectable reagent having high affinity for phosphatidyl serine preferably intact cells, detection occurring before or after an optional step for isolating apoptotic cells from non-apoptotic cells, which isolation can occur due to the fact that apoptotic cells have been provided with a detectable reagent having high affinity for phosphatidyl serine, the reagent also being selectable in a manner known per se. A suitable reagent having high affinity for phosphatidyl serine is a polypeptide or protein classified as an annexin. A kit for carrying out such methods is provided.

39 Claims, 2 Drawing Sheets

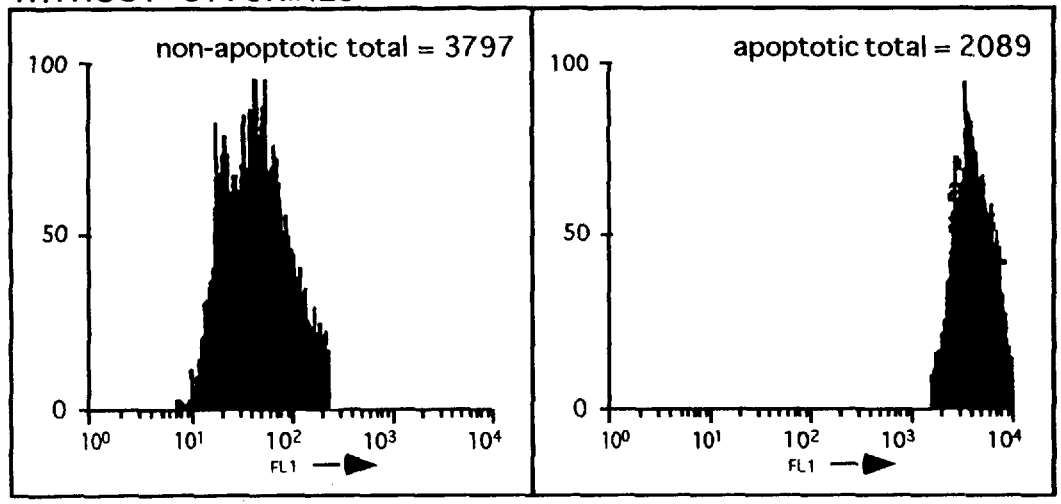
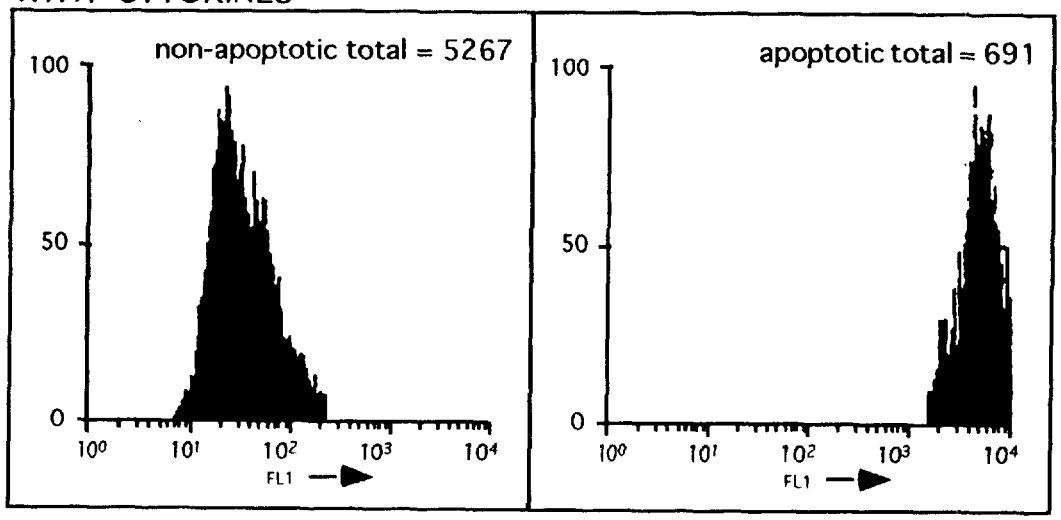

METHOD FOR DETECTING AND/OR OPTIONALLY QUANTIFYING AND/OR SEPARATING APOPTOTIC CELLS IN OR FROM A SAMPLE

This application is a U.S. national stage application of international application PCT/NL95/00134, filed on Apr. 11, 1995, and also claims priority benefit of European Patent Application 94200968.9, filed Apr. 11, 1994.

FIELD OF THE INVENTION

The subject invention lies in the field of medicine and pharmacology. In particular, the present invention relates to a procedure to measure apoptosis in physiology and pathology in order to support clinical diagnosis and to evaluate and monitor efficacies of drugs and therapies.

BACKGROUND OF THE INVENTION

The total number of cells of an organism is the result of processes, that lead to the formation of new cells (proliferation) on the one hand and processes, that lead to the breakdown of existing cells (cell death) on the other hand. Apoptosis is the major process responsible for the breakdown of existing cells (1).

Apoptosis is also known as programmed cell death or cell suicide, a process that is characterized by a sequence of distinct events ultimately leading to cell death. Cells, that enter into apoptosis, break up junctions with neighbouring cells if present. The cytoplasm condenses, the nucleus coalesces and breaks up into fragments. At the onset of apoptosis chromatin compacts and segregates against the nuclear envelope. Cytoplasm condenses and the nuclear and cellular membranes begin to convolute. In late stage apoptosis nuclear fragmentation occurs and the cell surface developes protuberances. Apoptotic bodies form that are phagocytosed by adjacent cells. During apoptosis the plasma membrane characteristics alter. For example a modification in carbohydrate composition and a change in membrane hydrophobicity and charge take place. The endoplasmic reticulum transforms into vesicles that fuse with the plasma membrane and loss of intracellular fluids and ions occurs. In that final stage the cell breaks up into a number of small apoptotic bodies.

Cell death through apoptosis affects single cells within a population in an unsynchronised manner and occurs rather inconspicuously without any inflammatory response (2).

Normal tissue homeostasis requires that for every cell that is added one must die. Apoptosis is an essential process of physiology and proceeds in a well regulated manner in homeostatic balance with its counterpart proliferation (3,4). If the processes of proliferation and apoptosis are out of balance this may result in pathogenesis. It is now becoming evident that an increasing number of pathological situations can be related to aberrant apoptosis. There is currently a lot of research directed at anti-cancer therapies as it is postulated that cancer occurs when cells refuse to die, i.e. when a defect in the apoptotic pathway occurs. An anti-cancer treatment would therefore consist of inducing naturally occurring suicide pathways to yield biotech cancer cures. Apoptosis is furthermore considered to be potentially relevant for a large number of diseases such as ischemia, stroke, heart disease and autoimmunity. It is considered to be such a fundamental biological phenomenon that the challenge is in fact to find a process it is not involved with (13). For example the macrophages dying in the lungs of patients suffering from cystic fibrosis are undergoing apoptosis. The lung-clogging viscosity of the DNA is characteristic of apoptotic death (12). Apoptosis has also been used as diagnostic in autoimmune diseases such as systemic lupus erythematosus (SLE) (13). B-cell malignancies such as B-cell leukemia lymphoma display growth of tumor cells not because of an increased proliferation rate but due to defective apoptosis. Tumor cell metastasis is succesful if apoptosis of the migrating tumor cells is suppressed. The ratio between the rate of proliferation and the rate of apoptosis of tumor cells determines the rate of tumor growth and hence its life threatening character.

From these considerations it is clear that modulation of apoptosis in vivo by drugs is a promising strategy for future anti-cancer therapies. In order to diagnose the proliferation: apoptosis ratio in tissue and in particular in tumors and to develop and guide therapies one has to have means to measure apoptosis in a quick and sensitive manner.

To date methods described in the literature fail to serve this purpose as they are elaborate and time consuming or have insufficient specificity.

Duvall et al. (7) describe how apoptotic or non-apoptotic populations can be separated by isopycnic centrifugation using a Percoll density gradient. As these gradients are associated with considerable cell loss comprising up to 60% of the total cells, and they do not remove all Trypan Blue positive cells from the apoptotic population this is a method that is not routinely used (Trypan Blue exclusion is used to determine how many cells are viable).

Fadok et al. (14) describe that the percentage of apoptotic cells in a lymphocyte population was determined by morphologic examination of cyto centrifuged cells stained with Diff-Quick (Baxter Healthcare Corp. Mc.Gaw Park. Ill.), the key characteristics of apoptosis being nuclear pyknosis and cytoplasmic condensation. Viability of the cells was determined by Trypan Blue exclusion. Fadok et al. (14) describe tests carried out that were directed at discovering how macrophages remove apoptotic lymphocytes by phagocytosis. They illustrated that phagocytosis of apoptotic lymphocytes was inhibited by the L-isoforms of compounds structurally related to phosphatidyl serine and that the membranes of apoptotic lymphocytes bound increased amounts of merocyanine 540 dye relative to those of normal cells indicating that their membrane lipids were more loosely packed consistent with a loss of membrane phospholipid asymmetry. The observations suggested that apoptotic lymphocytes lose membrane phospholipid asymmetry and expose phosphatidyl serine on the outer leaflet of the plasma membrane. Macrophages then phagocytose an apoptotic lymphocyte after recognition of the exposed phosphatidyl serine. The authors of the document were not concerned with specific detection or isolation of apoptotic cells. They used an aspecific dye for determination of the loose packaging of the membrane apoptotic cells. They discerned the difference between apoptotic and non-apoptotic cells by using isopycnic centrifugation or morphological analysis and followed this by colouring the cells with the aspecific merocyanine 540 dye that binds in a greater amount to loosely packed membranes. No suggestion is given regarding a novel method for specifically discriminating between apoptotic and non-apoptotic cells.

The golden standard up to now for determining the presence of apoptotic cells is the analysis of cellular DNA. For this method the cells are destroyed and the DNA is extracted and analyzed. Tell-tale DNA ladders of about 180 base pairs show up on gels of apoptotic cells. The presence of such ladders in a DNA assay have become the signal for diagnosis of, for example, autoimmune diseases such as systemic lupus erythematosus. Analysing DNA fragmentation can be carried out using the diphenylamine reaction of Burton (15) as modified by Sellens and Cohen (16) (6). The longstanding view that double-stranded DNA cleavage was the mechanism that delivered the coupe de grace to apoptotic cells as evidenced by the DNA ladders has been challenged recently. Researchers suggest that cells can undergo apoptosis without internucleosomal cleavage (17) and the implication is that apoptosis could be much more wide-spread than many of the present diagnostic tools suggest.

One of the other big problems in the field of apoptosis is that it is easy to make the mistake of thinking you have inhibited apoptosis if you have killed the cells first as you will not detect apoptotic cells but lysed cells. In looking for compounds or treatments which are capable of inhibiting apoptosis it is essential that the procedure should in fact inhibit apoptosis and not just simply kill the cells by another means before they reach the apoptotic state.

BRIEF DESCRIPTION OF THE DRAWINGS

FIG. 1 illustrates results of flow cytometry analysis of neutophils without addition of cytokines.

FIG. 2 illustrates results of flow cytometry analysis of neutrophils with addition of cytokines.

DESCRIPTION OF THE INVENTION

Figure 3:
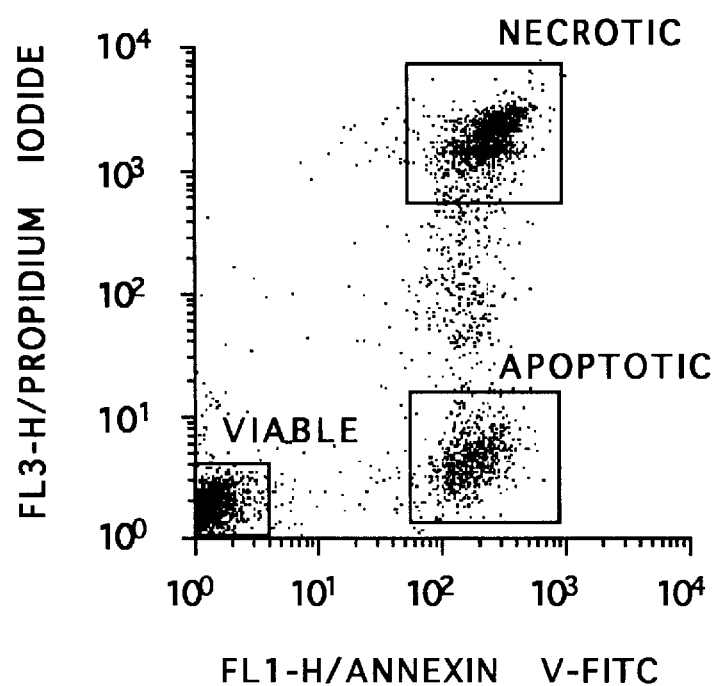
FIG. 3 illustrates a population distribution of viable, apoptotic and necrotic leukemic cells.

One of the features of apoptotic cells is an altered plasma membrane characteristic (7,8). It has surprisingly been discovered that intact cells that have entered the program of apoptosis change their membrane characteristics such that the membranes can bind increased amounts of a reagent having high affinity for phosphatidyl serine. High affinity in this context means having a dissociation constant for phosphatidyl serine $Kd<10^{-6}M$, preferably a $Kd<10^{-10}M$. Surprisingly good results can be obtained using polypeptides or proteins belonging to the category of the annexins. The light chain of Factor Va is another suitable example of a reagent having high affinity for phosphatidyl serine.

Annexins constitute a well described family of amphiphilic proteins which can bind reversibly to cellular membranes in the presence of cations (9). The primary structure of the annexins comprises a fourfold or eightfold repeated domain that contains a consensus sequence. A non-conserved and as such an annexin specific N-terminal tail precedes the first domain. The domains are interconnected via short variable linker peptides. Annexin proteins can be purified from tissues like placental tissue (10) or can be obtained via recombinant techniques (11).

In PCT/EP90/02257 annexins are described for binding to phosphatidyl serine on blood platelets that have entered the prothrombin activation state. Nothing is taught or suggested about using annexin for any other objective and no suggestion is given regarding the use in a method according to the invention.

The observation that apoptotic cells have an increased number of binding sites for annexins has lead to the development of assays, that discriminate rapidly between non-apoptotic and apoptotic cells on an individual basis without destroying the cells. The procedure is based on the following principle. Suspended cells or tissue sections can be mixed with a reagent specific for phosphatidyl serine and the amount of cell surface bound reagent can be measured either directly by virtue of a label conjugated to the reagent or indirectly via antibodies specific for the reagent. The parameter of cell-bound reagent discloses whether the cell is apoptotic or not. The determination can be of a qualitative or a quantitative nature.

It is also possible to separate apoptotic cells from non-apoptotic cells through selection of a marker conjugated to the reagent, which is suited for such a separation process. A number of markers suitable for selecting a specific population and isolating it from a different population are known in the state of the art.

In general the subject invention is directed at a method for detecting and/or optionally quantifying apoptotic cells in a sample comprising a) contacting the sample with a detectable reagent having high affinity for phosphatidyl serine and b) qualitatively and/or optionally quantitatively detecting intact cells that have reacted with the detectable reagent having high affinity for phosphatidyl serine. This method can also be used as part of a method for separating apoptotic cells in a sample. The method directed at separation of apoptotic cells is carried out by a) contacting the sample with a detectable reagent having high affinity for phosphatidyl serine and b) qualitatively and/or optionally quantitatively detecting intact cells that have reacted with the detectable reagent having high affinity for phosphatidyl serine, said detection occurring before or after step c) for separating apoptotic cells from non-apoptotic cells, which separation can occur due to the fact that apoptotic cells have been provided in step a) with the detectable reagent having high affinity for phosphatidyl serine, said detectable reagent also being selectable in a manner known per se. The detection of intact cells as opposed to cells that have undergone lysis can be carried out in a manner known per se. It is known for example that propidiumiodide is a marker that recognizes cells that have undergone lysis but does not recognize intact cells. After treatment with propidium iodide the intact cells can also be separated from cells that have undergone lysis in a manner known per se, such as through flow cytometry. In general a marker that does not bind to intact cells but does bind to cells that have undergone lysis can be used in a manner known per se to discern lysed from non lysed cells. Preferably the marker for lysed cells is also discernible from the marker for the reagent having high affinity for phosphatidyl serine and can also be used to actually separate a population of lysed cells from cells that are intact.

As stated above the reagent having high affinity for phosphatidyl serine can be a polypeptide or protein classified as an annexin. The specific phospholipid-binding properties of annexin in general and of annexin V in particular in combination with the ability to conjugate an annexin with a wide range of compounds in such a manner that the conjugate still possesses phospholipid-binding properties can be used to determine qualitatively and/or quantitatively cell apoptosis either occuring spontaneously or induced by any kind of environmental factor as a further embodiment of the method according to the subject invention. Any derivative of an annexin still exhibiting a high affinity for phosphatidyl serine can also be used in a method according to the invention. When using an annexin or a derivative thereof as the reagent having high affinity for phosphatidyl serine in a method according to the subject invention it is preferable to also contact the sample with the reagent having high affinity for phosphatidyl serine in the presence of a cation, preferably in the presence of a bivalent cation in order for the reagent to exhibit binding capacity with phosphatidyl serine. The bivalent cation can be selected for example from the group comprising $Cd^{2+}$, $Zn^{2+}$, $Mn^{2+}$, $Co^{2+}$ and preferably $Ca^{2+}$. In the presence of certain amounts of $Ca^{2+}$, for example annexin V adsorbs to phospholipid membranes in an extrinsic fashion. The $Ca^{2+}$ ions are believed to bridge between the protein molecule and the phospholipid membrane by binding to sites in annexin V and ligating to 6 carbonyl oxygens of specific amino acids. The thus chelated $Ca^{2+}$ ions however are unsaturated by coordination and charge. The 7th coordination site may then accept the phosphoryl moiety of phosphatidyl serine. The bridging appears to be very stable under physiological ionic strength and pH conditions and above threshold $Ca^{2+}$ levels but is disjointed rapidly and completely upon decreasing the $Ca^{2+}$ concentration below threshold level. Interestingly these threshold levels of $Ca^{2+}$ appear to be inversely related to the phosphatidyl serine content of the membrane. Annexin V in particular displays a high affinity for phosphatidyl serine containing membranes. Expression of the affinity with an objective parameter such as a Kd appears however to be difficult and is given as an estimation to be less than $10^{-10}M$. In practice this is reflected by the fact that no other phospholipid-binding proteins like the vitamin K dependent coagulation factors and the cofactors VII (a) and V(a) seriously compete with annexin V for binding to a membrane.

It is also possible to carry out the method according to the invention using a combination of two or more different cations. In particular the combination of $Ca^{2+}$ and $Zn^{2+}$ gives good results. It is also possible to use a trivalent cation, such as $Tb^{3+}$.

The reagent to be used must have a high affinity for phosphatidyl serine. It must also preferably not have such a high affinity for other membrane components that are available on the outer leaflet of cell membranes of non-apoptotic cells. In particular it should not bind very well to phosphatidylcholine or sphingomyelin and preferably should not bind very well to other outer membrane components of non-apoptotic cells. When the method according to the invention is to be used for comparative purposes merely to determine a qualitative effect this latter requirement is not stringent as one merely has to differentiate between the cells to which a large amount of reagent has been bound and cells to which a smaller amount of reagent has been bound. Naturally however the higher the affinity of the reagent is for phosphatidyl serine the better. Differentiation between the various phospholipids that are comprised in the outer membranes of non-apoptotic and apoptotic cells is what makes annexins ideal reagents for separating apoptotic cells from non-apoptotic cells. Any reagent that can specifically determine between phosphatidyl serine and phosphatidylcholine in favour of phosphatidyl serine can be used in a method according to the invention. An additional characteristic of the reagent having high affinity for phosphatidyl serine is that it can still be capable of binding phosphatidyl serine when it is conjugated to the label to be used for detection and/or selection.

The subject method now offers the means to analyse the results of certain treatments and/or compounds on apoptotic cells and also on the formation of apoptotic cells. It now becomes possible to follow the effects of the treatment and/or of compounds on the activation or inactivation of the pathway leading to apoptotic cells. It also makes a simple separation of apoptotic cells from non-apoptotic cells in a certain population possible without having to destroy the cells. The subsequently separated populations of apoptotic and non-apoptotic cells can then therefore also be used for further tests and/or clinical applications like transplantation of autologous or heterologous stem cells or bone marrow cells. It is also possible to analyse and isolate on an individual cell basis. The method according to the invention can be used on a sample of suspended cells or tissue sections.

The amount of reagent having high affinity for phosphatidyl serine bound per cell can be measured either directly or indirectly. In the case of a direct measurement the cells to be analysed are contacted with reagent having high affinity for phosphatidyl serine that carries a label. Such a label can be any generally acceptable detectable marker such as a fluorescent marker, a radioactive marker, an enzyme, a metal, a dye, a detectable immunoglobulin or a protein part. Suitable examples are radioactive marker selected from the group comprising $^{125}I$, $^{131}I$, $^{111}In$, $^{32}P$, $^{35}S$ and $^{99}Te$. Suitable fluorescent markers can be selected from the group comprising fluorescein, phycoerythrin and rhodamin. Suitable enzyme markers can be selected from the group comprising alcohol dehydrogenase, peroxidase and alkaline phosphatase. The protein part can be selected from the group ferritin, biotin, avidin and streptavidin and derivatives thereof. A suitable dye can be selected from the group comprising Evans Blue and Coomassie Brilliant Blue. Labeling procedures are specific for the type of label and are described in the literature or are provided by the commercial suppliers of the labels. The above-mentioned examples of labels are merely illustrations and any generally acceptable labels that are commercially available can be used.

For an indirect measurement the sample to be tested can be contacted with unlabeled reagent having high affinity for phosphatidyl serine and the amount of bound reagent can be determined by reagent specific antibodies in a manner known per se.

Measurement of apoptosis can be performed after contacting the sample with cations and an annexin protein for example. The measurement of the apoptosis can be carried out using standard techniques for the determination of the presence and/or amount of label. Examples of techniques that can be used for the analyses are flow- and image cytometry and image analysis. In the case of indirect measurement using antibodies any antibody detection immunoassays can be used that are described in the state of the art.

In particular the separation of apoptotic cells from a sample can occur using a reagent having high affinity for phosphatidyl serine conjugated to a fluorescent label followed by use of a Facs cell sorter system set to separate cells with a large amount of fluorescence from cells with low fluorescence or even no fluorescence. The separation can also occur through use of a solid phase that exhibits a high affinity for the reagent having high affinity for phosphatidyl serine or the conjugate form of the reagent that is used. For example immobilised biotin can be used to bind streptavidin conjugated to the reagent having high affinity for phosphatidyl serine.

The method according to the invention can be used for determining the effect of a compound or a specific treatment on the degree of apoptosis in an individual or particular sample. This determination of the effect can be ascertained by carrying out the method according to the invention with a sample that has been subjected to the presence of the compound to be tested or has been subjected to the treatment which is to be tested and comparing this result to the result obtained carrying out the method according to the invention under the same conditions with a standard sample or with a sample taken prior to the presence of the compound and/or prior to subjecting the sample to the treatment to be tested. This comparison can be of a qualitative or a quantitative nature.

A kit suitable for carrying out the method according to the invention also falls within the scope of the invention. Such a kit must comprise a reagent specific for phosphatidyl serine that is detectable or that can be made detectable even when the reagent is conjugated to phosphatidyl serine. The reagent can already have been provided with a label in the kit or a label can also be provided with the kit. The kit must also comprise a detectable and preferably selectable label capable of discerning between intact cells and cells that have undergone lysis. A suitable example of such a label is propidium iodide. Optionally the cation required for binding the reagent specific for phosphatidyl serine to the cell membrane can be included when the kit comprises an annexin as specific reagent for phosphatidyl serine. The kit can furthermore comprise media suitable for carrying out the method according to the invention. The kit can also comprise standard samples of specific cell populations which can be used in a comparative assay. The kit can be specific for the type of cell or the type of tissue that is to be analysed due to the presence of suitable media and/or labels for these specific cells. In the case of analyses of effects of pharmaceuticals for cancer treatment it is quite often the case that specific cancers are specific for certain tissues or cell types and in such cases it is interesting to use specific media or markers suitable for such cells.

EXAMPLE 1

Neutrophils are isolated from blood by standard techniques. The neutrophils are kept overnight in culture medium in the absence or presence of cytokines. Cytokines are known to prevent neutrophils from entering apoptosis.

In order to measure apoptosis in the neutrophil population, the cells are mixed with 3 mM $Ca^{2+}$ in buffered saline and 10 $\mu$g/ml final concentration of annexin V, conjugated with fluorescein and 10 $\mu$g/ml propidium iodide. The mixed cells are analysed by flow cytometry. FIG. 1 illustrating results of the test without addition of cytokines and FIG. 2 illustrating results of the test with cytokines illustrate that the propidium iodide negative cells contain 2 populations that are distinguishable by this method. A population of intact cells with a low amount of bound annexin V and a population of intact cells with a high amount of bound annexin V. The latter population appeared apoptotic as revealed by other analytical methods. From the flow cytometric analysis it followed that in the absence of cytokines the ratio of non-apoptotic cells to apoptotic cells is 1,82:1, whereas in the presence of cytokines this ratio is 7,62:1. This illustrates the fact that due to the cytokine presence the amount of cells entering the apoptotic phase is markedly lower. The effect of a different compound than a cytokine can be compared in a similar manner and thus the effect of such a compound on apoptosis can also be discerned rapidly and sensitively.

EXAMPLE 2

The wells of a microtitre plate are seeded with adherent cells in a manner known per se. The selection of the adherent cell type to be used will depend on the diagnosis to be carried out. A number of different cell types that are suitable are commercially available and the selections of the type to be used will be apparent to a person skilled in the art. The cells are subsequently treated in a manner potentially resulting in induction or inhibition of apoptosis. The extent of apoptosis is then assessed by addition of Annexin V e.g. conjugated with a reporter group such as fluorescein or biotin in a buffer containing $Ca^{+2}$ ions. After incubation the unbound Annexin V is washed away. The amount of bound Annexin V is then directly or indirectly measured. Direct measurement can occur in the case of Annexin V-fluorescein in a microplate reader. Indirect measurement can occur using streptavidin-horseradish peroxidase and a chromogenic substrate in combination with Annexin V-biotin. The amount of bound Annexin relates to the extent of apoptosis per well.

EXAMPLE 3

The present invention will hereinafter be described by examples as a tool to serve important clinical questions in the therapy of various diseases.

3.1. Evaluation of the efficacy of an anti-cancer therapy for a leukemic patient Blood is withdrawn from the patient under conditions that are not fatal to the white blood cells. Such conditions are described by public literature.

The blood is centrifuged to form a buffy coat, which contains the white blood cells. These are collected and centrifuged by density centrifugation e.g. Ficoll or Percoll of a desired density. The density chosen depends on the type of leukemia. The procedure is constructed to isolate highly enriched leukemic cells. The isolated leukemic cells are suspended in culture medium e.g. Iscove's DMEM, or RPMI1640. The medium can be supplemented with serum of human or bovine origin and with additives like glutamic acid, growth factors, cytokines or other modulators of cell physiology.

The suspended cells are placed in culture dishes and incubated at e.g. 37° C. The main components of possible anti-cancer therapies, like e.g. fludarabine, methotrexate, cyclosporine, are added in varying concentrations to the cells in culture. The cells are cultured further in the presence of the components. At predetermined time points samples are withdrawn and measured for cell death by the principle of the method of the present invention: A cell sample is washed with Hepes/NaCl buffer containing 0.5–5 mM $Ca^{+2}$-ions and finally suspended in 445 $\mu$l buffer containing approximately $10^4$–$10^6$ cells. 5 $\mu$l of Annexin V, conjugated with fluorescein, and 50 $\mu$l of propidium iodide are added to the sample resulting in e.g. 0.025–10 $\mu$g/ml and 0.5–20 $\mu$g/ml respectively. The sample is further incubated and then analysed by flow cytometric two-color analysis according to established procedures.

FIG. 3 illustrates a typical outcome of such analysis. This analysis gives the population distribution of viable, apoptotic and necrotic cells. The fraction of death cells (apoptotic+necrotic cells) is indicative for the efficacy of the drug used on this particular cell type. Hence, this assay reveals drug resistency of the leukemic cells of the patient and, thus guides the clinician in selecting an anti-cancer therapy.

3. II. Evaluation of the progression of AIDS

Blood is withdrawn from a HIV-positive subject or an AIDS patient under conditions that are not fatal to the white blood cells. Such conditions are described by public literature. The peripheral blood mononuclear cells (PBMC) are isolated by standard techniques including centrifugation to obtain a buffy coat and subsequently centrifugation of the buffy coat on a density gradient like e.g. Ficoll or Percoll of a desired density. The PBMC are suspended in culture medium e.g. Iscove's DMEM, or RPMI1640. The medium can be supplemented with serum of human or bovine origin and with additives like glutamic acid, growth factors, cytokines or other modulators of cell physiology. The suspended cells are placed in culture dishes and incubated at e.g. 37° C. At predetermined time points samples are withdrawn and measured for cell death by the principle of the method of the present invention. The cells are washed with phosphate buffered saline and then incubated with phycoerythrin labelled CD4 or CD8 antibody. The cells are then washed with Hepes/NaCl, containing 0.5–5 mM $Ca^{2+}$-ions. The cells are suspended in 445 µl of buffer containing e.g. $10^4$–$10^6$ cells. 5 µl of Annexin V, conjugated with fluorescein, and 50 µl or propidium iodide are added to the sample resulting in 0.025–10 µg/ml and 0.5–20 µg/ml respectively. The sample is further incubated and then analysed by flow cytometric three-color analysis according to established procedures. FIG. 3 illustrates a typical outcome of such analysis. This analysis gives the population distribution of viable, apoptotic and necrotic cells. Because of the three-color analysis it is possible to measure the percentage of death cells in the PMBC subsets CD4+ and CD8+. The percentage of death cells in these subpopulations of PBMC is indicative for the progression of AIDS and guides the clinician in the selection of therapy.

3. III. Evaluation of the status of the disease systemic lupus erythematosus

Blood is withdrawn from SLE patients and treated to obtain PMBC as described in example 3.II. The isolated PMBC are suspended in culture medium like p.e. Iscove's DMEM, or RPMI1640. The medium can be supplemented with serum of human or bovine origin and with additives like glutamic acids, growth factors, cytokines or other modulators of cell physiology. The suspended cells are placed in culture dishes and incubated at e.g. 37° C. At predetermined time points samples are withdrawn and measured for cell death by the principle of the method of the present invention.

The cells are then washed with Hepes/NaCl, containing 0.5–5 mM $Ca^{2+}$-ions. The cells are suspended in 445 µl of buffer containing e.g. $10^4$–$10^6$ cells. 5 µl of Annexin V, conjugated with fluorescein, and 50 µl of propidium iodide are added to the sample resulting in e.g. 0.025–10 µg/ml en 0.5–20 µg/ml respectively, the sample is further incubated and then analysed by flow cytometric two-color analysis according to established procedures.

FIG. 3 illustrates a typical outcome of such analysis. This analysis gives the population distribution of viable, apoptotic and necrotic cells. The fraction of death cells (apoptotic+necrotic cells) is indicative for the status of the activity of the disease and, hence, guides the clinician in selecting a method of treatment.

3.IV. Evaluation of normal or aberrant development of the embryo

Pregnant mice, from 11–13 days post conception (plug= day 0), are sacrificed by cervical dislocation after anesthesia with ether. The uterus is taken out, embryos are collected and divided into two groups. Embryos are temporary cultured for detection of cell death by injection of Annexin V, conjugated with biotin. Embryos are injected into the ventricle of the heart using a Hamilton-Syringe pipeting system with glass needles with a tip diameter of 15–25 µm. A volume of approximately 3 µm Annexin V-biotin solution is injected under a surgical microscope while the embryo is kept in buffer of 37° C. When successfully injected a temporary blanching of the umbilical vein will be seen. Heart activity is examined and embryos that survive a 30 minute period of incubation are further processed. After incubation embryos are fixed overnight in 4% Forman heaps buffer for Light Microscopy (LM) of in 2% glutaraldehyde-2% paraformaldehyde cacodylate buffer for Electron Microscopy at 4° C.

Histological Analysis for LM

Following fixation embryos are dehydrated, embedded in paraffin and serially sectioned at 3 µm. Endogenous peroxidase is blocked by incubation in methanol/$H_2O_2$ (9:1 v/v) for 20 minutes. Sections are washed in phosphate buffered saline (PBS). Cell bound Annexin V-biotin is detected using the avidin-biotin complex method with horseradish peroxidase conjugated avidin (avidin-HRP) (Vector ABC Elite kit, Brunschwig, Germany) at room temperature. Staining is developed with 3,3'-diaminobenzidinetetrahydrochloride (DAB) and counterstained with haematoxylin.

Histological Analysis for EM

After incubation with Annexin V-biotin, embryos are fixed by intra cardiac injection, using glass needles as previously described. Then tissue segments are removed and fixed overnight at 4° C. Sections of 100 µM are cut on a vibratome and staining of Annexin V-biotin is developed as for LM. After DAB, sections are postfixed with $OsO_4$ and stained with 3% uranylacetate in toto followed by dehydration and embedding in plastic (Durcopan). Tissue is cut in ultrathin slices on a microtome (Reichert Jung Ultracut S) and finally stained with 1% lead citrate. Sections are examined by electron microscopy.

Annexin V-biotin binds to dying or death cells and not to viable cells. Hence, the sections of the treated embryo will visualise the topology of cell death in the developing embryo at the time point of removal of the embryo's from the uterus. Cell death is programmed in the embryo by coordinates of space and time. Cell death aberrant by space and time will have consequences for the organism. Spina bifida e.g. is the result of the lack of cell death at a certain location at a certain time point. The inventory of normally programmed cell death is well described by public literature. This inventory functions as reference to judge the (ab)normality of the cell death in the developing embryo as measured by the method described in this example. Measurement of cell death in the developing embryo is of importance in studying genetic defects and the evaluation of the teratogenicity of compounds.

REFERENCES

1. Ellis, R. E., Yuan, J. and Horvitz, H. R. (1991)— Mechanisms and functions of cell death. Annu. Rev.Cell. Biol. 7 663–698.
2. Wyllie, A. H., Kerr, J. F. R. and Currie, A. R. (1980) Cell death: The significance of apoptosis. Int. Rev. Cytol. 68, 251–300.
3. Schwartzman, R. A. and Cidlowski, J. A. (1993) Apoptosis: The biochemistry and molecular biology of programmed cell death. Endocrine Reviews 14, 133–151.
4. Bursch, W., Oberhammer, F. and Schulte-Hermann, R. (1992)—Cell death by apoptosis and its protective role against disease. Trends Pharmacol. Sci. 13, 245–251.
5. Koury, M. J. (1992)—Programmed cell death in hematopoiesis. Exp. Hematol. 20, 391–394.
6. Wyllie, A. H. (1980)—Glucocorticoid-induced thymocyte apoptosis is associated with endogenous endonuclease activation. Nature 284, 555–556.
7. Duvall, E., Wyllie, A. H. and Morris, R. G. (1985)— Macrophage recognition of cells undergoing programmed cell death (apoptosis). Immunology 56, 351–358.
8. Morris, R. G., Duvall, E. D., Hargraeves, A. D. and Wyllie, A. H. (1984)—Hormone induced cell death. Surface changes in thymocytes undergoing apoptosis. Am. J. Pathol. 115, 426–436.
9. Creutz, C. E. (1992)—The annexins and exocytosis. Science, 258, 924–930.
10. Romisch, J. and Heimburger, N. (1990)—Purification and characterization of six annexins from human placenta. Biol. Chem. Hoppe-Seyler, 371, 383–388.
11. Maurer-Fogy, Reutelingsperger, C. P. M., Pieters, J., Bodo, G., Stratowa, C. and Hauptmann, R. (1988)—Cloning and expression of cDNA for human vascular anticoagulant, a Ca2+-dependent phospholipid binding protein. Eur. J. Biochem. 174, 585–592.
12. Bio/Technology 11: 580–582, May 1993
13. Bio/technology 11: 787–792, July 1993
14. Fadok et al.
15. Burton, K. 1956—A study of the conditions and mechanism of the diphenylamine reaction for the colorimetric estimation of deoxyribonucleic acid. Biochem. J. 62:315.
16. Sellins, K. S., and Cohen, J. J. 1987. Gene induction by gamma-irradiation leads to DNA fragmentation in lymphocytes. J. Immunol. 139:3199.
17. Tomei. D., Shapiro, J., and Cope, F. 1993. Apoptosis in C3H/101/2 mouse embryonic cells. Proc. Natl. Acad. Sci. USA 90:853–857.

I claim:

1. A method for detecting and optionally quantifying apoptotic cells in a sample, comprising:
   a) contacting cells in the sample with a detectable reagent having high affinity for phosphatidylserine indicated by a dissociation constant for phosphatidylserine, $Kd > 10^{-6} M$;
   b) detecting intact cells that have reacted with said detectable reagent; and
   c) if desired, quantifying the intact cells that have reacted with said detectable reagent.

2. A method for separating apoptotic cells from non-apoptotic cells in a sample, comprising:
   a) contacting cells in said sample with a detectable reagent having high affinity for phosphatidylserine indicated by a dissociation constant for phosphatidylserine, $Kd > 10^{-6} M$; and
   b) isolating intact cells that have reacted with said detectable reagent.

3. A method according to claim 2, wherein said detectable reagent is a selectable reagent and said apoptotic cells are isolated by selection of intact cells that have reacted with said selectable agent.

4. A method according to claim 3, wherein said apoptotic cells are separated from non-apoptotic cells by binding of said cells that have reacted with said selectable reagent to a solid phase that exhibits a high affinity for said selectable reagent that is bound to said apoptotic cells.

5. A method according to claim 4 wherein said selectable reagent is annexin or a conjugated form of annexin.

6. A method according to claim 1 or claim 2, wherein the reagent having high affinity for phosphatidylserine is a polypeptide or protein classified as an annexin.

7. A method according to claim 1 or claim 2, wherein cells that have undergone lysis are distinguished from intact cells by a detectable marker for cells that have undergone lysis.

8. A method according to claim 7 wherein said detectable marker is propidium iodide.

9. A method according to claim 7 wherein cells marked by said detectable marker for cells that have undergone lysis are detected through flow cytometry.

10. A method according to claim 1 or claim 2, wherein said detectable reagent is annexin V or a derivative thereof.

11. A method according to claim 1 or claim 2, wherein said detectable reagent is contacted with said sample in the presence of a cation which enhances the affinity of said detectable reagent for phosphatidylserine.

12. A method according to claim 11 wherein said cation is a bivalent cation.

13. A method according to claim 12, wherein said bivalent cation is selected from the group consisting of $Cd^{2+}$, $Zn^{2+}$, $Mn2+$, $Co^{2+}$, and $Ca^{2+}$.

14. A method according to claim 13 wherein said cation is $Ca^{2+}$.

15. A method according to claim 11, wherein said cation is $Tb^{3+}$.

16. A method according to claim 1 or claim 2, wherein said detectable reagent is contacted with said sample in the presence of both $Ca^{2+}$ and $Zn^{2+}$ which together enhance the affinity of said detectable reagent for phosphatidylserine.

17. A method according to claim 1 or claim 2, wherein said detectable reagent is provided with a detectable label.

18. A method according to claim 17 wherein said detectable label is selected from the group consisting of a fluorescent label, a radioactive label, an enzyme, a metal, a dye, a detectable immunoglobulin, a protein, and a detectable part of a protein.

19. A method according to claim 18, wherein said detectable label is a radioactive label selected from the group consisting of $^{125}I$, $^{131}In$, $^{32}P$, $^{35}S$, and $^{99}Tc$.

20. A method according to claim 18, wherein the said detectable label is a fluorescent label selected from the group consisting of fluorescein, phycoerythrin and rhodamine.

21. A method according to claim 18, wherein said detectable label is an enzyme selected from the group consisting of alcohol dehydrogenase, peroxidase and alkaline phosphatase.

22. A method according to claim 17, wherein said detectable label is selected from the group consisting of ferritin, biotin, avidin, streptavidin and derivatives thereof.

23. A method according to claim 17, wherein said detectable label is a dye selected from the group consisting of Evans Blue and Coomassie Brilliant Blue.

24. A method according to claim 1 or claim 2, wherein said cells that have reacted with said detectable reagent are detected by a flow cytometer or by an immunoassay for said detectable reagent.

25. A method according to claim 1 or claim 2, wherein, in the step of contacting said cells in said sample with said reagents, said cells are adherent cells that are adhered to a microtiter plate.

26. A method for determining the effect of a compound or a specific treatment on the degree of apoptosis in cells of an individual and/or cells in a cell sample comprising carrying out the method according to claim 1 or claim 2 with cells from said individual or with cells from said cell sample that have been subjected to said compound and/or to said treatment and comparing the extent of apoptosis in said cells to the extent of apoptosis obtained by carrying out the same method under the same conditions with a standard sample and/or with cells taken from said individual or from said cell sample prior to subjection of said individual or said cell sample to said compound and/or said treatment.

27. A method according to claim 1 wherein said apoptotic cells are detected in a sample comprising cells which are suitable for transplantation or a method according to claim 2 wherein said apoptotic cells are separated from non-apoptotic cells which are suitable for transplantation.

28. A method according to claim 27 wherein said cells which are suitable for transplantation are autologous or heterologous stem cells or bone marrow cells.

29. A method according to claim 1 or claim 2 wherein said detectable reagent is annexin V or a derivative thereof, and said intact cells that have reacted with said detectable reagent are distinguished from cells that have undergone lysis by contacting said cells in said sample with a detectable marker for cells that have undergone lysis.

30. A method according to claim 29 wherein said detectable marker is propidium iodide.

31. A method according to claim 30 wherein cells that have reacted with said detectable reagent and cells that are marked by said detectable marker are detected by flow cytometry.

32. A method according to claim 30 wherein cells that have reacted with said detectable reagent and cells that are marked by said detectable marker are detected by fluorescence microscopy.

33. A kit suitable for detecting and/or quantifying and/or isolating apoptotic cells comprising a detectable reagent having high affinity for phosphatidylserine indicated by a dissociation constant for phosphatidylserine, $K_d > 10^{-6} M$; and a detectable marker for cells that have undergone lysis.

34. A kit according to claim 33 wherein said detectable reagent is annexin V or a derivative thereof.

35. A kit according to claim 33 further comprising a cation which enhances the affinity of said detectable reagent for phosphatidylserine.

36. A kit according to claim 33 further comprising buffered saline solution suitable for contacting said detectable reagent and said detectable marker with cells and for detecting cells that react with said detectable reagent and cells which are marked by said detectable marker.

37. A kit according to claim 33 wherein said detectable marker is a selectable marker such that cells which are marked by said selectable marker can be separated from cells which are not marked by said selectable marker.

38. A kit according to claim 33 wherein said detectable marker is propidium iodide.

39. A kit according to claim 33 wherein said detectable reagent is annexin V or a derivative thereof and said detectable marker is propidium iodide.

* * * * *